United States Patent
Schmitt

(10) Patent No.: US 8,076,519 B2
(45) Date of Patent: Dec. 13, 2011

(54) ORGANIC-SULPHIDE COMPOSITION WITH MASKED ODOUR

(75) Inventor: Paul-Guillaume Schmitt, Lescar (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 12/844,006

(22) Filed: Jul. 27, 2010

(65) Prior Publication Data

US 2011/0024678 A1 Feb. 3, 2011

Related U.S. Application Data

(60) Provisional application No. 61/234,680, filed on Aug. 18, 2009.

(51) Int. Cl.
*C07C 315/06* (2006.01)

(52) U.S. Cl. .............. 568/18; 568/19; 568/21; 252/384

(58) Field of Classification Search ................ 568/18, 568/19, 21; 252/384
See application file for complete search history.

(56) References Cited

U.S. PATENT DOCUMENTS

| 5,559,271 | A * | 9/1996 | Shaw et al. | 568/21 |
| 2002/0156326 | A1* | 10/2002 | Fremy | 568/19 |
| 2008/0008729 | A1* | 1/2008 | Swaine et al. | 424/401 |

* cited by examiner

*Primary Examiner* — Mark Kopec
*Assistant Examiner* — Haidung Nguyen
(74) *Attorney, Agent, or Firm* — Steven D. Boyd

(57) ABSTRACT

The present invention relates to the masking of the odor of organic sulphides and more particularly that of alkyl sulphides or of dialkyl sulphides, especially dimethyl sulphide, and also of oxides thereof, and especially of dimethyl sulphoxide, by addition, to said organic sulphides, of at least one odor-masking agent comprising at least one monoester, at least one di- or triester, at least one alcohol, at least one ketone and, optionally, at least one terpene.

13 Claims, No Drawings

ORGANIC-SULPHIDE COMPOSITION WITH MASKED ODOUR

The present invention relates to the field of organic sulphides and more particularly that of alkyl sulphides or dialkyl sulphides, especially dimethyl sulphide (or dimethyl disulphide, or alternatively DMDS), and also that of the oxides thereof, and especially of dimethyl sulphoxide (or DMSO).

It is well known that organic sulphides have, in general, a strong, unpleasant, or even aggressive odour. In particular, DMDS has a strong and aggressive odour due in part to the presence of highly odorous impurities and in part to the garlicky and ethereal odour intrinsic to DMDS. The same is true of most organic sulphides. In general, the oxides of these organic sulphides, in particular DMSO, have a less aggressive odour, but, depending on the concentrations of impurities, this odour can, however, be unpleasant, and an impairment for the end user.

This strong odour hinders the increased growth of these products, for example in the case of DMDS, in applications such as the sulphurization of catalysts or as loading additive for steam cracking. However, in comparison with other products used in these applications, such as tert-alkyl polysulphides, DMDS exhibits numerous advantages, in particular a high sulphur content (68%) and non-coking degradation products ($CH_4$, $H_2S$). Furthermore, in these applications, DMDS results in performance levels that are generally superior to the other products, such as tent-alkyl polysulphides.

However, these other products may have odorous levels that are lower than that of DMDS and may, as a result, make their use preferred in certain cases.

Many processes for synthesizing organic sulphides and oxides thereof exist today. The most widely used, and the most cost-effective from an industrial point of view, have however the disadvantage of resulting in by-products responsible for the unpleasant odours of the final products.

For example, among the methods for synthesizing DMDS, a particularly effective and economical method is the oxidation of methyl mercaptan by sulphur according to the invention:

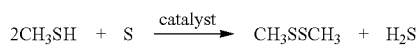

This oxidation of methyl mercaptan by sulphur, catalysed by organic or inorganic, homogeneous or heterogeneous, basic agents under batchwise or continuous conditions, is accompanied by a release of hydrogen sulphide and of dimethyl polysulphides ($CH_3S_xCH_3$) with a sulphur rank x of greater than 2.

In order to manufacture DMDS according to this process with high yields and a limited production of DMPS (dimethyl polysulphides with a rank greater than 2), patent EP 0 446 109, the content of which is incorporated herein by way of reference, describes a preparation process comprising two reaction regions interrupted by an intermediate degassing region and followed by a distillation region. Although giving a good performance level in terms of yield and selectivity for DMDS, it is found that this process results in a not insignificant amount of methyl mercaptan (MM, approximately 4000 ppm) and a very small amount of dimethyl sulphide (DMS, approximately 300 ppm), originating from the methyl mercaptan used or produced during the synthesis of DMDS, being left in the finished product.

The result of these volatile impurities is that they render the odour of the DMDS very unpleasant and aggressive and this strong odour is regarded as a significant cause of trouble during the handling of this product by users.

In order to mask the odour of organic polysulphides, U.S. Pat. No. 5,559,271 recommends adding thereto a certain amount of masking product such as, in particular, vanillin or ethyl vanillin. Although its general formula includes DMDS, this patent is more particularly directed towards the treatment of heavy polysulphides, such as, for example, di-tert-nonyl pentasulphide. The application of this method to DMDS does not enable its unpleasant odour to be effectively masked.

Patent EP 0 976 726 indicates that, in the specific case of DMDS having reduced contents of highly odorous volatile impurities such as methyl mercaptan and dimethyl sulphide, the most effective odour-masking agents are chosen from the esters of general formula $R^1CO_2R^2$ in which $R^1$ represents an optionally unsaturated, linear or branched hydrocarbon-based radical containing from 1 to 4 carbon atoms, and $R^2$ represents an optionally unsaturated, linear, branched or cyclic hydrocarbon-based radical containing from 2 to 8 carbon atoms.

The solutions known today for masking the odours of organic sulphides and oxides thereof are not, however, entirely satisfactory, and odour-masking agents which are more effective, and in particular for which the odour smelt by the final user is as pleasant as possible, are constantly being sought for these products.

Thus, the subject of the invention is, inter alia, a composition comprising:

a) at least one organic sulphide, optionally in oxide form, of general formula (1):

in which R is chosen from a linear or branched alkyl radical containing from 1 to 4 carbon atoms, and a linear or branched alkenyl radical containing from 2 to 4 carbon atoms; n is equal to 0, 1 or 2; x is an integer chosen from 0, 1, 2, 3 or 4, preferably x represents 1, 2, 3 or 4; R' is chosen from a linear or branched alkyl radical containing from 1 to 4 carbon atoms, and a linear or branched alkenylene radical containing from 2 to 4 carbon atoms or, only when n=x=0, a hydrogen atom; and b) at least one odour-masking agent comprising at least one monoester, at least one di- and/or triester, at least one alcohol, at least one ketone and, optionally, at feast one terpene.

According to one preferred embodiment, the odour-masking agent comprises:

b1) from 1% to 40% by weight of at least one monoester;
b2) from 10% to 70% by weight of at least one di- and/or triester;
b3) from 1% to 30% of at least one alcohol;
b4) from 0.5% to 20% of at least one ketone of formula $R^a$—CO—$R^b$, in which $R^a$ represents a linear or branched hydrocarbon-based chain containing from 1 to 6 carbon atoms, optionally comprising one or more unsaturation(s) in the form of one or more double bond(s), and $R^b$ represents a cyclic hydrocarbon-based chain or else a linear or branched hydrocarbon-based chain optionally, but preferably, substituted with a cyclic structure, $R^b$ containing from 6 to 12 carbon atoms, optionally comprising one or more unsaturation(s) in the form of one or more double bond(s) and being optionally substituted with one or more hydroxyl groups; and b5) optionally, up to 20% of at least one terpene.

In the description of the present invention, the percentages are indicated by weight, unless specifically otherwise mentioned. The percentages of b1, b2, b3, b4 and b5 are percentages by weight expressed relative to the total weight of the odour-masking agent b). Unless otherwise mentioned, "ppm" means parts per million by weight.

According to one embodiment, the component a) used in the composition according to the present invention is an organic sulphide, optionally in oxide form, obtained according to any process known per se, or else commercially available, and preferably with a reduced content of volatile impurities. Such impurities are, for example, methyl mercaptan (MM) and dimethyl sulphide (DMS) in the case of DMDS; as regards DMSO, the impurities most commonly encountered are, for example, DMS, DMDS and/or BMTM (bis(methylthio)methane, also known as 2,4-dithiapentane).

Any method known to those skilled in the art for removing, or at the very least reducing, the abovementioned volatile impurities may be suitable; among said methods, mention may be made, in a nonlimiting manner, of distillation, evaporation under a stream of inert gas such as nitrogen, air and the like.

In particular, the amounts of MM and of DMS present in the DMDS may advantageously be greatly reduced by distillation. This method has the advantage of jointly removing the MM and the DMS, whereas the usual methods for odour reduction are generally based on the elimination of the residual mercaptans by specific reaction of the mercaptan function with an eliminating agent such as a base or an alkene oxide in the presence of a base. These methods would have no effect on the DMS present in the DMDS.

According to one preferred embodiment, the residual contents of MM and DMS, after topping of the DMDS, do not exceed 100 ppm and 50 ppm, respectively, by weight relative to the DMDS. The residual content of methyl mercaptan (MeSH) in the DMDS should not exceed 500 ppm by weight.

In the case of DMSO, the contents of impurities, such as DMS, DMDS and/or BMTM, should advantageously be less than 100 ppm, preferably less than 50 ppm, more preferably less than 10 ppm, for each of the impurities taken separately.

In one embodiment, the component a) of the composition according to the present invention corresponds to formula (1a):

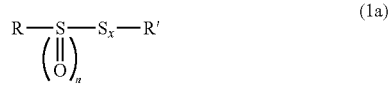

(1a)

in which R and R', which may be identical or different, are chosen from a linear or branched alkyl radical containing from 1 to 4 carbon atoms, and a linear or branched alkenyl radical containing from 1 to 4 carbon atoms; n is equal to 0; and x is an integer chosen from 1, 2, 3 or 4, preferably 2, 3 or 4.

Preferably, the component a) of formula (1a) is DMDS.

In another embodiment, the component a) of the composition according to the present invention corresponds to formula (1b):

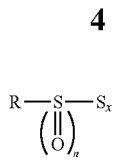

(1b)

in which R and R', which may be identical or different, are chosen from a linear or branched alkyl radical containing from 1 to 4 carbon atoms, and a linear or branched alkenyl radical containing from 1 to 4 carbon atoms; n is equal to 0, 1 or 2; and x is equal to 0.

Preferably, the component a) of formula (1b) is DMSO.

According to the invention, the masking of the odour of the organic sulphide or of the organic sulphides, and/or of the oxide form(s) thereof, corresponding to formula (1) described above, is obtained by addition, to said sulphides or oxides, of a composition defined in b) above.

The present invention has the advantage of masking the unpleasant odour of at least one organic sulphide and/or of the oxide(s) thereof, without chemically modifying the nature thereof. Thus, the present invention proposes a composition comprising a) a predominant amount of at least one organic sulphide of formula (1) defined above, to which a minor amount of a composition b) masking the unpleasant odour of the component a) is added.

The composition with masked odour according to the present invention may be prepared according to any process known per se by simply combining at least one component a) with at least one odour-masking composition b). It is, for example, possible to add at least one composition b) to at least one component a), or vice versa, optionally with stirring and/or optionally with heating. More generally, any known mixing and/or heating method may be used.

The preparation of the composition according to the invention may, for example, be carried out under atmospheric pressure, at a temperature of between 0° C. and 100° C., preferably between ambient temperature and approximately 80° C. The preparation may also be carried out under pressure or at a reduced pressure, at temperatures within the ranges indicated above.

The period of time required for the preparation of the composition with masked odour according to the invention varies according to the nature and the amount of the component(s) a) and of the composition(s) b) but also as a function of the temperature and of the pressure selected. As a general rule, this period corresponds to the period of time necessary for obtaining a homogeneous mixture and producing the desired effect of masking the odour of the component(s) a); it is generally between a few seconds and a few minutes, or even one or more hours.

The preparation process mentioned above can be prepared batchwise (batch process) or else continuously.

The composition b) is mixed, according to any method known to those skilled in the art, with the component a) in an amount ranging from a few ppm, for example 10 ppm, to 2%, preferably from 10 ppm to 1% by weight relative to the total weight of the composition. The amount of masking agent (composition b)) can vary to a large extent within the range indicated above, depending on the desired effect, the strength of the odour to be masked, the respective residual contents of the various impurities that may be present in the component(s) a) defined above, and the like.

Amounts of masking agent of less than a few ppm may be too small to obtain the desired effect. Amounts of masking agent greater than 2% may have harmful effects depending on the applications envisaged for the organic sulphides and/or oxides.

In the case of DMDS, for example, one of the principal advantages of this organic sulphide is the high sulphur content (68%). Too great a content of masking agent in the composition would result in a decrease in this sulphur titre and would reduce the advantage of this product in its principal applications.

Preferably, and by way of nonlimiting example, the content of odour-masking agent(s) b) is between 0.001% and 0.5% by weight relative to the total weight of the composition, and more particularly between approximately 0.1% and 0.5% by weight, advantageously equal to approximately 0.3%, in particular when the organic sulphide of which it is desired to mask the odour is DMDS.

Also by way of nonlimiting example, in the case of DMSO, the maximum content of odour-masking agent(s) is advantageously between 0.001% and 0.2% by weight relative to the total weight of the composition, preferably between 100 ppm and 1000 ppm, for example approximately 500 ppm by weight.

As indicated above, the composition according to the present invention comprises at least one composition of odour-masking agent b), said agent comprising from 1% to 40%, preferably from 2% to 35%, more preferably from 5% to 30% by weight, relative to the total weight of the composition b), of at least one monoester mentioned in b1).

As illustrative but nonlimiting examples of monoesters mentioned in b1), mention may be made of saturated or unsaturated $C_2$-$C_{20}$ acid esters, such as ethyl, propyl, butyl, pentyl, 2-methylbutyl, isoamyl, hexyl, benzyl, phenylethyl, menthyl or carvyl acetates, propionates, butyrates, methylbutyrates, pentanoates, hexanoates, heptanoates, caproates, oleates, linoleates and linolenates, and the like, and also mixtures thereof.

Isoamyl acetate, hexyl acetate, 2-methylbutyl butyrate, isoamyl butyrate, benzyl acetate, phenylethyl acetate and mixtures of these compounds are more particularly preferred.

The odour-masking agent composition b) also comprises at least one di- and/or triester b2), in an amount of between 10% and 70% by weight, preferably between 15% and 65% by weight, more preferably between 20% and 60% by weight, such as, in a nonlimiting manner, at least one di- and/or triester chosen from ortho-phthalates, such as diethyl ortho-phthalate; citrates, such as triethyl citrate; and malonates, such as diethyl malonate.

The odour-masking agent b) also comprises from 1% to 30%, preferably from 5% to 25% by weight relative to the total weight of the composition, of at least one alcohol b3), advantageously at least one monoalcohol containing from 1 to 30 carbon atoms, preferably from 6 to 20 carbon atoms, more preferably from 8 to 11 carbon atoms, said carbon atoms forming a linear or branched chain optionally comprising one or more unsaturation(s) in the form of one or more double bond(s), and optionally comprising a 5- or 6-membered cyclic structure which is saturated or completely or partially unsaturated.

The alcohols defined above are preferably monoalcohols, the hydroxyl function preferably being borne by an $sp^2$ carbon atom. It should be understood that the hydroxyl function may also be borne by a carbon atom included in a cyclic structure as defined above.

The alcohols used in the odour-masking agent and as defined above are advantageously, and by way of nonlimiting examples, chosen from menthol, neomenthol, phenylethyl alcohol, benzyl alcohol, citronellol, dihydromyrcenol, dihydroterpineol, dimetol, ethyllinalol, geraniol, linalol, tetrahydrolinalol, tetrahydromyrcenol, nerol, and the like, and also mixtures of two or more thereof.

The ketone or the ketones indicated in b4) above are chosen, by way of nonlimiting examples, and preferably, from damascones, damascenones, ionones, irisones, methylionones, frambinone (CAS No. 5471-51-2), and the like, and also mixtures thereof. The amount of ketone(s) is advantageously between 0.5% and 20%, preferably between 1% and 10% by weight relative to the total weight of the composition.

The odour-masking agent may optionally also comprise up to 20%, preferably from 1% to 10% by weight relative to the total weight of the composition, of at least one terpene.

As examples of terpenes, indicated in b5), which can be used, mention may be made, in a nonlimiting manner, of terpinenes, myrcene, limonene, terpinolene, pinenes, sabinene, camphene, and the like, mixtures of two or more thereof, and also essences based on terpenes, in particular those comprising these ingredients.

In addition, the odour-masking agent that can be used in the context of the present invention may comprise, in minor amounts, other agents (fragrances) customarily used in the perfumery field, and in particular one or more compounds bearing cyclic ketone and/or aldehyde function(s), among which mention may be made, in a nonlimiting manner, of geranial, neral, citronellal, menthone, isomenthone, 1,8-cineole, ascaridole, flavonone, and mixtures thereof.

The composition b) intended to mask the odour of the organic sulphides, and as described above, may, where appropriate, or if necessary, also comprise one or more additives commonly used in the field. Such additives may, for example, be chosen, in a nonlimiting manner, from solvents, pigments, dyes, preservatives, biocides and the like.

Among the solvents, most particularly preferred examples are alcohols, ethers, esters and glycols. Particularly advantageously, the solvent is chosen from diethyl phthalate, ethylene glycol, propylene glycol, diethylene glycol, dipropylene glycol, polyethylene glycols, polypropylene glycols, and mixtures thereof, and even more advantageously from diethyl phthalate, dipropylene glycol, and mixtures thereof.

It should be understood that a monoester, diester or triester present in the odour-masking agent composition b), as component b1) and/or b2), may also have the functions of the solvents defined above.

A typical odour-masking agent composition suitable for organic sulphides and oxide forms thereof, according to the present invention, comprises by weight:

from 5% to 30% by weight of at least one monoester b1), chosen from isoamyl acetate, ethyl 2-methyl butyrate, isoamyl butyrate, phenylethyl acetate, ethyl caproate, benzyl acetate, hexyl acetate and mixtures thereof;

from 20% to 60% by weight of at least one di- and/or triester b2) chosen from ortho-phthalates, such as diethyl ortho-phthalate; citrates, such as triethyl citrate; and malonates, such as diethyl malonate, and mixtures thereof;

from 5% to 25% of at least one alcohol, preferably of at least two alcohols, more preferably of at least three alcohols, as described above in b3);

from 1% to 10% of at least one ketone, preferably at least two ketones, more preferably at least three ketones, as described above in b4); and from 1% to 10% of at least one, preferably at least two, preferably a mixture of, terpene(s) referenced above in b5).

This composition, denoted Ci in the rest of the present disclosure, is most particularly suitable for masking the odour, or for improving the odour, of DMDS. This same composition Ci may also be advantageously used for masking or improving the odour of DMSO.

A representative but nonlimiting example of such a composition Ci is reproduced below, in which each of the components comprises one, several, or even all the compounds listed:

Component b1) 16.00%
comprising benzyl acetate, hexyl acetate,
isoamyl acetate, phenylethyl acetate,
ethyl caproate, ethyl 2-methyl butyrate
Component b2) 50.00%
comprising diethyl malonate, diethyl
phthalate
Component b3) 20.60%
comprising phenylethyl alcohol, citronellol,
geraniol, linalol, cis-3-hexenol
Component b4) 4.50%
comprising 1-(4-hydroxyphenyl)butan-3-one,
alpha-irisone
Component b5) 7.00%
orange terpenes
Others 1.90%
comprising citral, ethylmaltol, ethylmethyl
phenylglycidate These compositions are given by way of examples and are in no way restrictive with regard to the potential diversity of compositions permitted by the present invention defined by means of the attached claims.

The following examples illustrate the invention without limiting it.

EXAMPLE 1

DMDS Composition with Masked Odour

In order to characterize a fragrancing composition making it possible to mask or improve the odour of DMDS, an olfactory test procedure was set up. This procedure makes it possible to classify various formulations hedonically.

Operating Conditions:

In order to carry out this olfactory test, 30-litre polyethylene (PE) drums are used, each equipped with a lid in which a trap door of approximately 10 cm×10 cm is cut, allowing an operator (panelist) to smell the vapours contained in the drum.

A crystallizing dish containing two sheets of absorbent paper (chromatography paper) is placed in each of the drums. 1 ml of test composition is poured onto each sheet. The drums are stored closed for 24 hours at ambient temperature. The evaluation is subsequently carried out blind.

The panelists, of which there are ten, come in turn to test a few products per session (a maximum of three products per session). They begin by smelling the drum containing the reference DMDS for this study, and then one of the test compositions.

The panelists assign, according to their preference, a score to each of the test compositions, relative to the reference which arbitrarily received the score 5. The scores given by the panelists range from 1 (the most pleasant product) to 10 (the most unpleasant product).

Preparation of the Test Samples:

The DMDS, without odour-masking agent, is an industrial DMDS produced by Arkema, has a purity of greater than 99.7% and contains less than 100 ppm of methyl mercaptan and less than 50 ppm of dimethyl sulphide.

Added to this DMDS are 3000 ppm of a fragrancing composition having the following composition: 25% isoamyl acetate, 50% diethyl ortho-phthalate, 15% 2-methylbutyl butyrate and 10% benzyl acetate, as described in patent EP 0 976 726. This sample is the reference sample for the olfactory test and is called: A1.

3000 ppm of the fragrancing composition Ci according to the invention and defined above are added to the same industrial DMDS produced by Arkema without odour-masking agent. This sample is called: A2.

Results:

The results of the olfactory test are reproduced in table 1 below:

TABLE 1

| Test sample | Mean | Standard deviation | Group |
|---|---|---|---|
| $A_1$ | 5 | 0 | A |
| $A_2$ | 2.83 | 0.96 | B |

Statistical treatment of these results makes it possible to calculate the standard deviation and to classify the samples in two groups by studying the SSD (Smallest Significant Difference) given in this test at 0.87.

The SSD test is a statistical test for comparison of means and makes it possible to determine whether or not the means of two samples are significantly different, from a statistical point of view.

In the examples of the present invention, the statistical condition used is fixed at 95%. If the means are not significantly different, the two samples are classified in the same group. If the means are significantly different, the two samples constitute two separate groups (A and B in the examples that illustrate the invention).

The same operation is carried out in order to compare all the samples, thereby making it possible, ultimately, to obtain one, two or more groups, each constituting samples of which the mean scores are not significantly different. These various treatments are carried out using the FIZZ software, version 2.01 (Biosystèmes, Couternon, France).

There is therefore a very significant statistical difference indicating a much more pleasant perception of the odour of the sample $A_2$ than of the sample $A_1$.

EXAMPLE 2

DMSO Composition with Masked Odour

An olfactory test similar to that described in example 1 is carried out, taking DMSO as base, in place of DMDS.

Preparation of the Test Samples:

The reference DMSO is an industrial DMSO with a purity equal to 99.97%, produced by Arkema, and then supplemented with 50 ppm of dimethyl sulphide (DMS). This sample is called B1.

700 ppm of the fragrancing composition Ci according to the invention are added to the same batch of DMSO supplemented with 50 ppm of dimethyl sulphide. This sample is called B2.

The results of the olfactory test are reproduced in table 2 below:

TABLE 2

| Test sample | Mean | Standard deviation | Group |
|---|---|---|---|
| $B_1$ | 5.93 | 1.33 | A |
| $B_2$ | 2.75 | 1.52 | B |

As for example 1, the statistical treatment of these results makes it possible to calculate the standard deviation and to classify the samples in two groups by studying the SSD (Smallest Significant Difference) given in this test at 1.01.

There is therefore a very significant statistical difference indicating a much more pleasant perception of the odour of the sample B2 than of the sample B1.

EXAMPLE 3

DMSO Composition with Masked Odour

The same industrial DMSO as that of example 2, with a purity of 99.97%, produced by Arkema, is tested without the addition of the 50 ppm of DMS, according to the olfactory test described in example 2. This sample is called C1.

150 ppm of the fragrancing composition Ci according to the invention are added to this same industrial DMSO. This sample is called C2.

The results of the olfactory test on C1 and C2 indicate that the sample C2 is judged to be statistically much more pleasant than the sample $C_1$.

The invention claimed is:

1. Composition comprising:
   a) at least one organic sulphide, optionally in oxide form, of general formula (1):

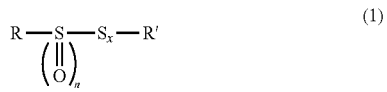

in which R is chosen from a linear or branched alkyl radical containing from 1 to 4 carbon atoms, and a linear or branched alkenyl radical containing from 2 to 4 carbon atoms; n is equal to 0, 1 or 2; x is an integer chosen from 0, 1, 2, 3 or 4, R' is chosen from a linear or branched alkyl radical containing from 1 to 4 carbon atoms, and a linear or branched alkenylene radical containing from 2 to 4 carbon atoms or, only when n=x=0, a hydrogen atom; and
   b) at least one odour-masking agent comprising at least one monoester, at least one di- and/or triester, at least one alcohol, at least one ketone and, optionally, at least one terpene.

2. Composition according to claim 1, in which the component a) is chosen from dimethyl disulphide and dimethyl sulphoxide.

3. Composition according to claim 1, in which the odour-masking agent comprises:
   b1) from 1% to 40% by weight of at least one monoester;
   b2) from 10% to 70% by weight of at least one di- and/or triester;
   b3) from 1% to 30% of at least one alcohol;
   b4) from 0.5% to 20% of at least one ketone of formula $R^a$—CO—$R^b$, in which $R^a$ represents a linear or branched hydrocarbon-based chain containing from 1 to 6 carbon atoms, optionally comprising one or more unsaturation(s) in the form of one or more double bond(s), and $R^b$ represents a cyclic hydrocarbon-based chain or else a linear or branched hydrocarbon-based chain optionally, substituted with a cyclic structure, $R^b$ containing from 6 to 12 carbon atoms, optionally comprising one or more unsaturation(s) in the form of one or more double bond(s) and being optionally substituted with one or more hydroxyl groups; and
   b5) optionally, up to 20% of at least one terpene.

4. Composition according to claim 3, in which the odour-masking agent b) comprises from 1% to 40% by weight, relative to the total weight of the composition, of at least one monoester b1), chosen from saturated or unsaturated $C_2$-$C_{20}$ acid esters, such as ethyl, propyl, butyl, pentyl, 2-methylbutyl, isoamyl, hexyl, benzyl, phenylethyl, menthyl or carvyl acetates, propionates, butyrates, methylbutyrates, pentanoates, hexanoates, heptanoates, caproates, oleates, linoleates and linolenates, and mixtures thereof.

5. Composition according to claim 3, in which the odour-masking agent b) comprises at least one di- and/or triester b2), in an amount of between 10% and 70% by weight, chosen from ortho-phthalates, citrates and malonates.

6. Composition according to claim 3, in which the odour-masking agent b) comprises from 1% to 30% by weight relative to the total weight of the composition b), of at least one alcohol b3), advantageously at least one monoalcohol containing from 1 to 30 carbon atoms, said carbon atoms forming a linear or branched chain optionally comprising one or more unsaturation(s) in the form of one or more double bond(s), and optionally comprising a 5- or 6-membered cyclic structure which is saturated or completely or partially unsaturated.

7. Composition according to claim 6, in which the alcohol is chosen from menthol, neomenthol, phenylethyl alcohol, benzyl alcohol, citronellol, dihydromyrcenol, dihydroterpineol, dimetol, ethyllinalol, geraniol, linalol, tetrahydrolinalol, tetrahydromyrcenol, nerol, and the like, and mixtures of two or more thereof.

8. Composition according to claim 3, in which the odour-masking agent b) comprises between 0.5% and 20 relative to the total weight of the composition b), of at least one ketone b4) chosen from damascones, damascenones, ionones, irisones, methylionones and frambinone, and mixtures thereof.

9. Composition according to claim 3, in which the odour-masking agent b) optionally comprises up to 20% by weight relative to the total weight of the composition, of at least one terpene b5), chosen from terpinenes, myrcene, limonene, terpinolene, pinenes, sabinene, camphene, and the like, mixtures of two or more thereof, and also essences based on terpenes, in particular those comprising these ingredients.

10. Composition according to claim 3, in which the odour-masking agent comprises by weight:
   from 5% to 30% by weight of at least one monoester b1), chosen from isoamyl acetate, ethyl 2-methyl butyrate, isoamyl butyrate, phenylethyl acetate, ethyl caproate, benzyl acetate, hexyl acetate and mixtures thereof;
   from 20% to 60% by weight of at least one di- and/or triester b2) chosen from ortho-phthalates, citrates and malonates, and mixtures thereof;
   from 5% to 25% of at least one alcohol, b3);
   from 1% to 10% of at least one ketone, b4); and
   from 1% to 10% of at least one, terpene(s), b5).

11. Composition according to claim 1, in which the masking agent b) is present in an amount ranging from 10 ppm to 2% by weight relative to the total weight of the composition.

12. Composition according to claim 1, in which the organic sulphide a) is dimethyl disulphide and the amount of odour-masking agent b) is between 0.001% and 0.5% by weight relative to the total weight of the composition.

13. Composition according to claim 1, in which the organic sulphide a) is dimethyl sulphoxide and the amount of odour-masking agent b) is between 0.001% and 0.2% by weight relative to the total weight of the composition.

* * * * *